United States Patent
Herwig et al.

(10) Patent No.: US 6,313,297 B1
(45) Date of Patent: Nov. 6, 2001

(54) BASE-CATALYZED SYNTHESIS OF 1-ARYL-4-(ARYL ETHYL)PIPERAZINES FROM AROMATIC OLEFINS AND 1-ARYLPIPERAZINES

(75) Inventors: Jürgen Herwig, Hünxe; Matthias Beller, Rostock; Claudia Breindl, München, all of (DE)

(73) Assignees: Aventis Research & Technologies (DE); GmbH & Co. KG (DE)

( * ) Notice: Subject to any disclaimer, the term of this patent is extended or adjusted under 35 U.S.C. 154(b) by 0 days.

(21) Appl. No.: 09/600,274

(22) PCT Filed: Dec. 19, 1998

(86) PCT No.: PCT/EP98/08344

§ 371 Date: Jun. 13, 2000

§ 102(e) Date: Jun. 13, 2000

(87) PCT Pub. No.: WO99/36412

PCT Pub. Date: Jul. 22, 1999

(30) Foreign Application Priority Data

Jan. 17, 1998 (DE) .............................................. 198 01 597

(51) Int. Cl.[7] .................. C07D 295/02; C07D 292/023; C07D 295/04
(52) U.S. Cl. ........................... 544/392; 544/393; 544/394
(58) Field of Search .................................... 544/392, 393, 544/394

(56) References Cited

FOREIGN PATENT DOCUMENTS 85 503    12/1965   (FR) .

OTHER PUBLICATIONS

Beller, Matthias, et al, *Tetrahedron* 54:6359–6368, "Base–Catalyzed Hydroamination of Aromatic Olefins—An Efficient Route to 1–Aryl–4–(Arylethyl) Piperazines" (1998).

*Primary Examiner*—Richard L. Raymond
(74) *Attorney, Agent, or Firm*—Connolly Bove Lodge & Hutz LLP

(57) ABSTRACT

A process for preparing a 1-aryl-4-(arylethyl)piperazine of the formula (I)

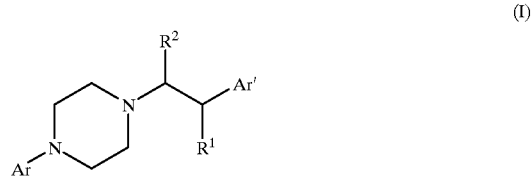

by reacting a 1-arylpiperazine of the formula (II)

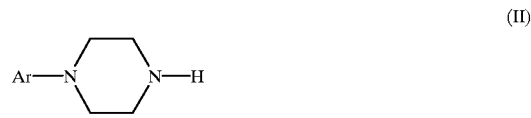

with an aromatic olefin of the formula (III)

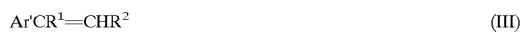

in an inert solvent in the presence of at least one basic catalyst, where in the formulae (I) to (III)

Ar and Ar' independently of one another are an aryl radical, selected from the group of the fused and unfused $C_6$–$C_{22}$-aromatics and the fused or unfused $C_5$–$C_{22}$-heteroaromatics which have at least one nitrogen, oxygen or sulfur atom in the ring; and $R_1$ and $R_2$ independently of one another are a hydrogen atom, a $C_1$–$C_8$-alkyl radical or an aryl radical Ar.

11 Claims, No Drawings

BASE-CATALYZED SYNTHESIS OF 1-ARYL-4-(ARYL ETHYL)PIPERAZINES FROM AROMATIC OLEFINS AND 1-ARYLPIPERAZINES

This application is a 371 of PCT/EP98/08344, filed Dec. 19, 1998.

The present invention relates to a novel process for preparing 1-aryl-4-(arylethyl)piperazines.

Arylpiperazines are, as building blocks for a large number of pharmaceutically active compounds, of industrial interest. In this context, 1-aryl-4-(arylethyl)piperazines are of particular importance as active compounds in medicinal chemistry. Thus, this class of compounds is the subject of a large number of patents and publications.

1-aryl-4-(arylethyl)piperazines are mainly prepared by reacting the corresponding arylpiperazines with 1-arylethyl-2-bromide. Another route is the reaction of anilines with N,N-bis-2-chloroethylanilines.

In both reaction routes, halogenated starting materials are used, giving stoichiometric amounts of salt by-products. The latter is ecologically disadvantageous. In addition, the alkylations are insufficiently selective, so that product yields of only 50–70% are obtained.

It is an object of the present invention to provide a process for preparing 1-aryl-4-(arylethyl)piperazines from simple starting materials under mild reaction conditions which can be carried out on an industrial scale and does not produce any salt by-products.

This object is achieved by a process for preparing a 1-aryl-4-(arylethyl)piperazine of the formula (I)

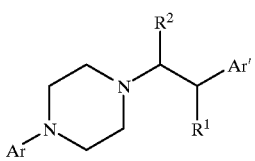

(I)

by reacting a 1-arylpiperazine of the formula (II)

(II)

with an aromatic olefin of the formula (III)

$$Ar'CR^1=CHR^2 \quad (III)$$

in an inert solvent in the presence of at least one basic catalyst, where in the formulae (I) to (III)

Ar and Ar' independently of one another are an aryl radical, selected from the group of the fused and unfused $C_6$–$C_{22}$-aromatics and the fused or unfused $C_5$–$C_{22}$-heteroaromatics which have at least one nitrogen, oxygen or sulfur atom in the ring; and $R_1$ and $R_2$ independently of one another are a hydrogen atom, a $C_1$–$C_8$-alkyl radical or an aryl radical Ar.

It is furthermore possible to prepare the product of the formula (I) by extending the intermolecular coupling between the aromatic olefin of the formula (III) and the arylpiperazine of the formula (II) by an intramolecular amination of a corresponding compound.

It is an essential property of the process according to the invention that, for the first time, the arylpiperazines react with aromatic olefins under base catalysis, generally in good to very good yields of from 90 to 99%. Salt by-products are not formed.

The inert solvent can be selected from the group consisting of aromatic hydrocarbons, such as toluene, xylenes, anisole, tetraline, and aliphatic ethers, such as tetrahydrofuran, dimethoxyethane, dioxane, tetrahydropyran, formaldehyde acetals. Examples of the aryl radical Ar are phenyl, naphthyl, anthryl, phenanthryl and diphenyl, pyridyl, furfuryl or pyrazolyl radicals.

The basic catalyst can be selected from the group consisting of alkali metal and alkaline earth metal hydrocarbons, such as, for example, phenyllithium or butyllithium;

alkali metal and alkaline earth metal amides, such as, for example, potassium amide, potassium dimethylamide, potassium diisopropylamide, potassium propylamide, potassium isopropylamide, sodium amide, sodium dimethylamide, sodium diisopropylamide, sodium propylamide, sodium isopropylamide, lithium amide, lithium dimethylamide, lithium diisopropylamide, lithium propylamide or lithium isopropylamide;

alkali metals and alkaline earth metals, such as, for example, sodium or potassium; and alkali metal hydrides, such as, for example, sodium hydride or potassium hydride.

In addition, the basic catalyst used can also be a mixture of the catalysts described above with one another or with alkali metal or alkaline earth metal silazides, such as, for example, potassium hexamethyidisilazide, sodium hexamethyldisilazide, lithium hexamethyidisilazide.

Preferred basic catalysts are alkali metal and alkaline earth metal hydrocarbons and alkali metal and alkaline earth metal amides.

Studies have shown that alkali metal amides and alkali metal hydrocarbons are particularly effective catalysts.

The basic catalyst can be employed directly in the form of one of the compounds mentioned or similar compounds. However, in some cases it is advantageous, owing to the stability of the basic catalyst, to prepare the active compound in situ from suitable precursors.

The basic catalyst can be employed in an amount of from 0.01 to 20 mol %, in particular from 0.1 to 5 mol %, based on the arylpiperazine of the formula (II).

The aryl radicals Ar or Ar' in the formulae (I) and (III) can, independently of one another, have up to 8 identical or different substituents from the group consisting of hydrogen, fluorine, chlorine, bromine or iodine atoms and $C_1$–$C_8$-alkyl, $C_1$–$C_8$-alkoxy, $C_1$–$C_8$-acyloxy, HO—, $O_2N$—, CN—, HOC(O)—, HC(O)—, HOS(O)$_2$—, $R^4S(O)_2$—, $R^4S(O)$—, $H_2N$—, $R^4N(H)$—, $R^4_2N$—, $R^4C(O)N(H)$—, $R^4C(O)$—, (OCH)HN—, Ar"C(O)—, ArC(O)O—, $CF_3$—, $H_2NC(O)$—, $R^4OC(O)C(H)=C(H)$—, Ar"$_2P(O)$—, $R^4_2P(O)$—, $R^4_3Si$— or heteroaryl radicals having 5 or 6 atoms in the aryl ring, where $R^4$ is a $C_1$–$C_{12}$-alkyl radical and Ar" is selected from the group of the fused or unfused $C_6$–$C_{22}$-aromatics and the fused or unfused $C_5$–$C_{22}$-heteroaromatics which have at least one nitrogen, oxygen or sulfur atom in the ring.

The reaction is carried out at temperatures of from 0 to 200° C., in particular at from 10 to 150° C. and preferably at from 20 to 120° C.

Owing to the tendency to undergo oligomerization or polymerization side reactions, it may, in the case of some aromatic olefins of the formula (III), be advantageous to add a polymerization inhibitor. For this purpose, it is possible to employ the customary polymerization inhibitors, such as, for example, p-quinone.

The examples below serve only to illustrate the process.

EXAMPLES

General Section

All reactions are carried out with exclusion of air and water under an atmosphere of argon in a 30 ml pressure tube from Aldrich with Teflon seal. The solvents used were dried by customary methods known from the literature and stored over 4 Å molecular sieves under an atmosphere of argon. Before use, all starting materials were dried and likewise stored over 4 Å molecular sieves and under protective gas. $^1$H-NMR (400 MHz) and $^{13}$C-NMR (100 MHz) spectra are calibrated by means of the chemical shifts of the solvents used.

General Procedure (Hereinbelow GP):

In a pressure tube, heated thoroughly and flushed with argon, 2.22 mmol of substituted N-arylpiperazine and 50 μl of hexadecane are initially charged and dissolved in 4 ml of THF. In the closed pressure tube, the solution is cooled with a mixture of isopropanol and dry ice for 30 min, and 5 mol % of n-butyllithium n-BuLi (1.6 molar n-BuLi solution in n-hexane) are then added under a stream of argon, whereupon the color of the solution in each case turns to yellow to orange. The mixture is then stirred for a further 30 min until it has warmed to ambient temperature again. 2.22 mmol of olefin are then added, and the reaction mixture is stirred vigorously at ambient temperature for 5 min. The mixture is heated at an oil bath temperature of 120° C. for 20 h and, after cooling, hydrolyzed with 2 ml of water. To isolate the product, the turbid two-phase system is admixed with 5 ml of 1 M hydrochloric acid and 5 ml of methylene chloride. The aqueous phase is separated off and the organic phase is extracted three times with in each case 5 ml of 1 M hydrochloric acid, and all aqueous phases are then combined and neutralized by addition of sodium carbonate. The neutral solution is extracted five times with in each case 5 ml of methylene chloride, and all organic phases are combined, and then washed repeatedly with water and dried over magnesium sulfate, and the solvent is removed under reduced pressure. Final isolation of the product is carried out by column chromatography.

Example 1

According to GP, 2.22 mmol (=0.40 g) of 1-(4-fluorophenyl)piperazine and 2.22 mmol (=0.23 g=0.25 ml) of styrene are reacted with 5 mol % (=0.111 mmol=70 μl) of n-BuLi solution. Column-chromatographic separation with ethyl acetate/n-hexane (3:1) gives the product 1-(4-fluorophenyl)-4-(2-phenyl-1-ethyl)piperazine as a light-brown solid.

| Yield | 99% of theory |
|---|---|
| Molecular weight | 284.38 g/mol |
| $R_f$ value | 0.53 (ethyl acetate/hexane 3:1) |

$^1$H-NMR (400 MHz, CDCl$_3$, 25° C.): δ=2.55–3.30 (m, 12H, aliphat. H); 6.80–6.95 (m, 4H, arom. arylpiperazine-H); 7.10–7.25 (m, 5H, arom. phenyl-H). $^{13}$C-NMR (100 MHz, CDCl$_3$, 25° C.): δ=34.0 (—CH$_2$-phenyl); 50.6 (—(CH$_2$)$_2$—N—CH$_2$—); 53.6 (—(CH$_2$)$_2$—N—CH$_2$—); 60.8 (—(CH$_2$)$_2$—N-aromatic); 115.8–116.0 (d, $^2$J$_{C,F}$=22 Hz, —CH—C—F); 118.2–118.3 (d, $^3$J$_{C,F}$=8 Hz, —CH—CH—C—F); 126.5; 128.8; 129.1; 140.5 (quart.-phenyl); 148.3 (quart. C—N—); 156.4–158.8 (d, $^1$J$_{C,F}$=239 Hz, C—F). GC-MS: m/e=284 (M$^+$), 207 [M$^+$-phenyl], 193 [M$^+$—CH$^2$-phenyl], 150, 122, 70,

Example 2

According to GP, 2.22 mmol (=0.40 g) of 1-(4-fluorophenyl)piperazine and 2.22 mmol (=0.30 g=0.30 ml) of para-methoxystyrene are reacted with 5 mol % (=0.111 mmol=70 μl) of n-BuLi solution. Column-chromatographic separation with ethyl acetate gives the product 1-(4-fluorophenyl)-4-[2-(4-methoxyphenyl)-1-ethyl]piperazine as a light-yellow solid.

| Yield | 77% of theory |
|---|---|
| Molecular weight | 314.41 g/mol |
| $R_f$ value | 0.60 (hexane/ethyl acetate 3:1) |

$^1$H-NMR (400 MHz, CDCl$_3$, 25° C.): δ=2.55–2.80 (m, 8H, —(CH$_2$)$_2$—N—CH$_2$—CH$_2$—); 3.07–3.16 (m, 4H, —(CH$_2$)$_2$—N-aromatic); 3.72 (s, 3H, —OCH$_3$); 6.75–6.80 (d, $^2$J=8.50 Hz, 2H, —CH—C—OCH$_3$); 6.80–6.95 (m, 4H, —CH—CH—C—F); 7.06–7.12 (d, $^2$J=8.50 Hz, —CH—CH—C—OCH$_3$). $^{13}$C-NMR (100 MHz, CDCl$_3$, 25° C.): δ=34.1 (—CH$_2$-C-phenyl); 50.5 (—(CH$_2$)$_2$—N—CH$_2$—); 53.6 (—(CH$_2$)$_2$—N—CH$_2$—); 55.7 (OCH$_3$); 61.1 (—CH$_2$—N-aromatic); 114.3 (—CH—C—OCH$_3$); 115.8–116.0 (d, $^2$J$_{C,F}$=22 Hz, —CH—C—F); 118.2–118.3 (d, $^3$J$_{C,F}$=8 Hz, —CH—CH—C—F); 125.3 (—CH—CH—C—OCH$_3$); 130.0 (quart. C-phenyl); 156.4–158.4 (d, $^1$J$_{C,F}$=199 Hz, —C—F). GC-MS: m/e=314 (M$^+$), 193 [M$^+$—CH$_2$-phenyl—OCH$_3$], 150, 122, 95 [phenyl-F$^+$].

Example 3

According to GP, 2.22 mmol (=0.40 g) of 1-(4-fluorophenyl)piperazine and 2.22 mmol (=0.34 g) of 2-vinylnaphthalene are reacted with 5 mol % (=0.111 mmol=70 μl) of n-BuLi solution. Column-chromatographic separation with ethyl acetate/n-hexane (1:1) gives the product 1-(4-fluorophenyl)-4-[2-(2-naphthyl)-1-ethyl]piperazine as a light-yellow solid.

| Yield | 84% of theory |
|---|---|
| Molecular weight | 334.44 g/mol |
| $R_f$ value | 0.59 (hexane/ethyl acetate 1:1) |

$^1$H-NMR (400 MHz, CDCl$_3$, 25° C.): δ=2.51–2.73 (m, 6H, —(CH$_2$)$_2$—N—CH$_2$—); 2.92–3.01 (m, 2H, —(CH$_2$)$_2$—N—CH$_2$—CH$_2$—); 3.03–3.15 (m, 4H, —(CH$_2$)$_2$—N-aromatic); 6.79–6.93 (m, 4H, —CH—CH—C—F); 7.27–7.32 (dd, $^2$J=8.0 Hz, $^3$J=1.5 Hz, 1H, aromatic H); 7.34–7.42 (m, 2H, aromatic H); 7.57–7.62 (s, 1H, aromatic H); 7.68–7.77 (m, 3H, aromatic H). $^{13}$C-NMR (100 MHz, CDCl$_3$, 25° C.): δ=34.1 (—CH$_2$-phenyl); 50.6 (—(CH$_2$)$_2$—N—CH$_2$—); 53.6 (—(CH$_2$)$_2$—N—CH$_2$—); 60.7 (—CH$_2$—N-aromatic); 115.8–116.0 (d, $^2$J$_{C,F}$=22 Hz, —CH—C—F); 118.2–118.3 (d, $^3$J$_{C,F}$=8 Hz, —CH—CH—C—F); 125.7–128.8 (aromatic C); 132.5, 134.0 (quart. C-naphthyl); 138.0 (quart. —CH$_2$—C-naphthyl); 148.3 (quart. C—N—); 156.4–158.8 (d, $^1$J$_{C,F}$=239 Hz, C—F). GC-MS: m/e=334 (M$^+$), 193 [M$^+$—CH$_2$-naphthyl], 150, 122, 95 [phenyl-F$^+$], 70,

Example 4

According to GP, 2.22 mmol (=0.39 g) of 1-(3-methylphenyl)piperazine and 2.22 mmol (=0.23 g=0.25 ml) of styrene are reacted with 5 mol % (=0.111 mmol=70 μl) of n-BuLi solution. Column-chromatographic separation with ethyl acetate gives the product 4-(2-phenyl-1-ethyl)-1-(3-tolyl)piperazine as a light-brown solid.

| Yield | 99% of theory |
|---|---|
| Molecular weight | 280.41 g/mol |
| $R_f$ value | 0.66 (hexane/ethyl acetate 3:1) |

$^1$H-NMR (400 MHz, CDCl$_3$, 25° C.): δ=2.24 (s, 3H, —CH$_3$); 2.57–2.66 (m, 6H, —(CH$_2$)$_2$—N—CH$_2$—); 2.76–2.83 (m, 2H, —(CH$_2$)$_2$—N—CH$_2$—CH$_2$—); 3.13–3.20 (m, 4H, —(CH$_2$)$_2$—N-aromatic); 6.60–6.71 (s and 2 d, 3H, $^2$J=8.00 Hz, —N-aromatic-H); 7.06–7.10 (t, $^2$J=8.00 Hz, 1H, —N-aromatic-H); 7.10–7.25 (m, 5H, —CH$_2$-phenyl-H). $^{13}$C-NMR (100 MHz, CDCl$_3$, 25° C.): δ=22.2 (—CH$_3$); 34.0 (—CH$_2$-phenyl); 49.6 (—(CH$_2$)$_2$—N—CH$_2$—); 53.8 (—(CH$_2$)$_2$—N—CH$_2$—); 60.9 (—CH$_2$—N-aromatic); 113.6, 117.3, 121.1, (C-tolyl); 126.5, 128.8, 129.1 (C-phenyl); 129.3 (C-tolyl); 139.2 (quart. C—CH$_3$); 140.6 (quart. C-phenyl); 151.7 (quart. C—N). GC-MS: m/e=280 [M$^+$], 189 [M$^+$—CH$_2$-phenyl], 146, 91 [phenyl-F$^+$], 70,

Example 5

According to GP, 2.22 mmol (=0.51 g) of 1-(3-trifluoromethylphenyl)piperazine and 2.22 mmol (=0.23 g=0.25 ml) of styrene are reacted with 5 mol % (=0.111 mmol=70 μl) of n-BuLi solution. Column-chromatographic separaton with ethyl acetate/n-hexane (1:1) gives the product 4-(2-phenyl-1-ethyl)-1-(3-trfluoromethylphenyl)piperazine as a yellow oil.

| Yield | 89% of theory |
|---|---|
| Molecular weight | 334.38 g/mol |
| $R_f$ value | 0.62 (hexane/ethyl acetate13:1) |

$^1$H-NMR (400 MHz, CDCl$_3$, 25° C.): δ=2.62–2.78 (m, 6H, —(CH$_2$)$_2$—N—CH$_2$—); 2.85–2.96 (m, 2H, —(CH$_2$)$_2$—N—CH$_2$—CH$_2$—); 3.26–3.38 (m, 4H, —(CH$_2$)$_2$—N-aromatic); 7.08–7.41 (m, 9H, aromatic H). $^{13}$C-NMR (100 MHz, CDCl$_3$, 25° C.): δ=34.1 (—CH$_2$-phenyl); 49.2 (—(CH$_2$)$_2$—N—CH$_2$—); 53.6 (—(CH$_2$)$_2$—N—CH$_2$—); 60.1 (—CH$_2$—N-aromatic); 112.6–112.7 (q, $^3$J$_{C,F}$=4 Hz, —CH—CH—C—CF$_3$); 115.3–115.5 (q, $^3$J$_{C,F}$=4 Hz, —N—C—CH—C—CF$_3$); 119.1; 120.8–128.9 (q, $^1$J$_{C,F}$=273 Hz, —CF$_3$); 126.7, 129.0, 129.2 (C-phenyl); 130.1; 131.4–132.6 (q, $^2$J$_{C,F}$=19 Hz, —C—CF$_3$); 140.6 (quart. C-phenyl); 151.9 (quart. C—N—). GC-MS: m/e= 334 [M$^+$], 243 [M$^+$—CH$_2$-phenyl], 200, 172, 145 [phenyl-CF$_3$$^+$], 105, 91, 70,

Example 6

According to GP, 2.22 mmol (=0.43 g) of 1-(2-methoxyphenyl)piperazine and 2.22 mmol (=0.23 g=0.25 ml) of styrene are reacted with 5 mol % (=0.111 mmol=70 μl) of n-BuLi solution. Column-chromatographic separation with ethyl acetate/n-hexane (1:2) gives the product 1-(2-methoxyphenyl)-4-(2-phenyl-1-ethyl)piperazine as a yellow oil.

| Yield | 95% of theory |
|---|---|
| Molecular weight | 296.41 g/mol |
| $R_f$ value | 0.48 (hexane/ethyl acetate 1:1) |

$^1$H-NMR (400 MHz, CDCl$_3$, 25° C.): δ=2.62–2.89 (m, 6H, —(CH$_2$)$_2$—N—CH$_2$—); 2.80–2.89 (m, 2H, —(CH$_2$)$_2$—N—CH$_2$—CH$_2$—); 3.07–3.19 (m, 4H, —(CH$_2$)$_2$—N-aromatic); 3.37 (s, 3H, —OCH$_3$); 6.83–7.03 (m, 4H, arylpiperazine-H); 7.17–7.33 (m, 5H, phenyl-H). $^{13}$C-NMR (100 MHz, CDCl$_3$, 25° C.): δ=34.0 (—CH$_2$-phenyl); 51.5 (—(CH$_2$)$_2$—N—CH$_2$—); 53.8 (—(CH$_2$)$_2$—N—CH$_2$—); 55.7 (—OCH$_3$); 61.0 (—CH$_2$—N-aromatic); 111.6, 118.6, 121.4, 123.3 (C-aromatic-arylpiperazine); 126.5, 128.8, 129.1 (C-phenyl); 140.7 (quart. C-phenyl); 141.7 (quart. C—N—); 152.7 (quart. C—OCH$_3$). GC-MS: m/e=296 [M$^+$], 205 [M$^+$—CH$_2$-phenyl], 190 [M$^+$—CH$_3$—CH$_2$-phenyl], 162, 120, 105, 91, 70,

Example 7

According to GP, 2.22 mmol (=0.40 g) of 1-(4-fluorophenyl)piperazine and 2.22 mmol (=0.31 g=0.28 ml) of 4-chlorostyrene are reacted with 5 mol % (=0.111 mmol= 70 μl) of n-BuLi solution. Column-chromatographic separation with ethyl acetatein-hexane gives the product 1-(4-fluorophenyl)-4-[2-(4-chlorophenyl)-1-ethyl]piperazine as a light-yellow solid.

| Yield | 98% of theory |
|---|---|
| Molecular weight | 318.83 g/mol |
| $R_f$ value | 0.53 (ethyl acetate) |

$^1$H-NMR (400 MHz, CDCl$_3$, 25° C.): δ=2.51–2.82 (m, 6H, —(CH$_2$)$_2$—N—CH$_2$—); 3.09 (dd, 2H, —(CH$_2$-phenyl); 3.12–3.29 (m, 4H, —(CH$_2$)$_2$—N-aromatic); 6.76–6.95 (m, 4H, F-arylpiperazine-H); 7.08 (d, 2H, J=8.50 Hz, aromatic H); 7.17–7.23 (m, 2H, aromatic H). $^{13}$C-NMR (100 MHz, CDCl$_3$, 25° C.): δ=32.9 (—CH$_2$-phenyl); 50.2 (—(CH$_2$)$_2$—N—CH$_2$—); 53.2 (—(CH$_2$)$_2$—N—CH$_2$—); 60.1 (—CH$_2$—N-aromatic); 115.4–115.6 (d, J=22 Hz, —CH—C—F); 117.8–117.9 (d, J=8 Hz, —CH—CH—C—F); 128.5, 130.0 (C-chloroaromatic); 131.8 (quart. C—Cl); 138.7 (quart. C-chloroaromatic); 147.9 (quart. C—N—); 156.0158.4 (d, J=238 Hz, —C—F). GC-MS: m/e=318 [M$^+$], 193 [M$^+$—CH$_2$—Cl-phenyl], 178, 150, 122, 95, 70, 42, 28,

| EA | Calc. | C 67.81 | H 6.32 | N 8.79 |
|---|---|---|---|---|
|  | Found | C 67.57 | H 6.45 | N 8.97 |

Example 8

According to GP, 2.22 mmol (=0.36 g=0.34 ml) of phenylpiperazine and 2.22 mmol (=0.26 g=0.30 ml) of 3-methylstyrene are reacted with 5 mol % (=0.111 mmol=70 μl) of n-BuLi solution. Column-chromatographic separation with ethyl acetate/n-hexane (3:1) gives the product 1-phenyl-4-[2-(3-methylphenyl)-1-ethyl]piperazine as a light-yellow solid.

| Yield | 93% of theory |
| --- | --- |
| Molecular weight | 280.42 g/mol |
| $R_f$ value | 0.77 (hexane/ethyl acetate 3:1) |

$^1$H-NMR (400 MHz, CDCl$_3$, 25° C.): δ=2.52 (s, 3H, —CH$_3$); 2.82–2.95 (m, 6H, —(CH$_2$)$_2$—N—CH$_2$—); 3.01 (m, 2H, —(CH$_2$)$_2$—N—CH$_2$—CH$_2$—); 3.48 (m, 4H, —(CH$_2$)$_2$—N-aromatic); 7.03–7.27 (m, 6H); 7.39 (t, 1H, J=7.00 Hz); 7.48 (t, 2H, J=7.50 Hz). $^{13}$C-NMR (100 MHz, CDCl$_3$, 25° C.): δ=21.4 (—CH$_3$); 33.5 (—CH$_2$-phenyl); 49.2 (—(CH$_2$)$_2$—N—CH$_2$—); 53.2 (—(CH$_2$)$_2$—N—CH$_2$—); 60.6 (—CH$_2$—N-aromatic); 116.0; 119.7; 125.7; 126.8; 128.3; 129.1; 129.5; 138.0 (quart. C-phenyl); 140.1 (quart. C—CH$_3$); 151.3 (quart. C—N—). GC-MS: m/e=280 [M$^+$], 151, 137, 129,

| Elemental analysis | Calc. | C 81.38 | H 8.63 | N 9.99 |
| --- | --- | --- | --- | --- |
| | Found | C 81.01 | H 8.48 | N 9.84 |

Example 9

According to GP, 2.22 mmol (=0.36 g=0.34 ml) of phenylpiperazine and 2.22 mmol (=0.26 g=0.29 ml) of α-methylstyrene are reacted with 5 mol % (=0.111 mmol=70 μl) of n-BuLi solution. Column-chromatographic separation with ethyl acetate/n-hexane (3:1) gives the product 1-phenyl-4-(2-phenylpropyl)piperazine as a light-yellow solid.

| Yield | 86% of theory |
| --- | --- |
| Molecular weight | 280.42 g/mol |
| $R_f$ value | 0.70 (hexane/ethyl acetate 3:1) |

$^1$H-NMR (400 MHz, CDCl$_3$, 25° C.): δ=1.33 (d, 3H, J=7.00 Hz, —CH$_3$); 2.53–2.72 (m, 6H, —(CH$_2$)$_2$—N—CH$_2$—); 3.03 (sextet, 1H, J=7.00 Hz, —CH—); 3.15–3.25 (m, 4H, —(CH$_2$)$_2$—N-aromatic); 6.86 (t, 1H, J=7.00 Hz, p-H-arylpiperazine); 6.93 (d, 2H, J=8.00 Hz, o-H-arylpiperazine); 7.20–7.35 (m, 7H). $^{13}$C-NMR (100 MHz, CDCl$_3$, 25° C.): δ=20.0 (—CH$_3$); 37.4 (—CH-phenyl); 49.1 (—(CH$_2$)$_2$—N—CH$_2$—); 53.5 (—(CH$_2$)$_2$—N—CH$_2$—); 66.1 (—CH$_2$—N-aromatic); 115.0; 119.5; 126.1; 127.2; 128.3; 129.0; 146.1 (quart. C-phenyl); 151.4 (quart. C—N—). GC-MS: m/e=280 [M$^+$], 175 [M$^+$—CH$_3$—CH-phenyl], 160 [M+—CH$_3$—CH-phenyl, —CH$_3$], 132, 104, 70, 56, 28,

| Elemental analysis | Calc. | C 81.38 | H 8.63 | N 9.99 |
| --- | --- | --- | --- | --- |
| | Found | C 81.37 | H 8.65 | N 9.82 |

Example 10

According to GP, 2.22 mmol (=0.36 g=0.34 ml) of phenylpiperazine and 2.22 mmol (=0.26 g=0.29 ml) of β-trans-methylstyrene are reacted with 5 mol % (=0.111 mmol=70 μl) of n-BuLi solution. Column-chromatographic separation with ethyl acetate/n-hexane (3:1) gives the product 1-phenyl-4-(1-methyl-2-phenylethyl)piperazine as a yellow solid.

| Yield | 71% of theory |
| --- | --- |
| Molecular weight | 280.42 g/mol |
| $R_f$ value | 0.56 (hexane/ethyl acetate 3:1) |

$^1$H-NMR (400 MHz, CDCl$_3$, 25° C.): δ=0.97 (d, 3H, J=6.50 Hz, —CH$_3$); 2.42 (dd, 1H, J=12.50 Hz, J=9.00 Hz, —CH$_2$—CH—); 2.76 (m, 4H, —(CH$_2$)$_2$—N—CH$_2$—); 2.84 (m, 1H, —CH—CH$_3$); 3.00 (dd, 1H, J=13.00 Hz, J=4.00 Hz, —CH$_2$—CH—); 3.19 (m, 4H, —(CH$_2$)$_2$—N-aromatic); 6.82 (t, 1H, J=7.00 Hz, p-H-arylpiperazine); 6.91 (d, 2H, J=8.00 Hz, o-H-arylpiperazine); 7.11–7.27 m, 7H). $^{13}$C-NMR (100 MHz, CDCl$_3$, 25° C.): δ=14.4 (—CH$_3$); 39.4 (—CH-phenyl); 48.5 (—(CH$_2$)$_2$—N—CH$_2$—); 49.6 (—(CH$_2$)$_2$—N—CH—); 61.3 (—CH$_2$—N-aromatic); 116.1; 119.6; 125.8; 128.2; 129.1; 129.3; 140.5 (quart. C-phenyl); 151.5 (quart. C—N—). GC-MS: m/e=280 [M$^+$], 189 [M$^+$—CH$_2$-phenyl], 174 [M+—CH$_2$-phenyl, —CH$_3$], 160, 132, 120, 91, 56, 28.

| Elemental analysis | Calc. | C 81.38 | H 8.63 | N 9.99 |
| --- | --- | --- | --- | --- |
| | Found | C 81.57 | H 8.76 | N 9.75 |

What is claimed is:

1. A process for preparing a 1-aryl-4-(arylethyl)piperazine of the formula (I)

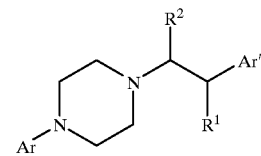

(I)

which comprises reacting a 1-arylpiperazine of the formula (II)

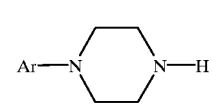

(II)

with an aromatic olefin of the formula (III)

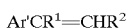

Ar'CR$^1$=CHR$^2$    (III)

in an inert solvent in the presence of at least one basic catalyst, where in the formulae (I) to (III)

Ar and Ar' independently of one another are an aryl radical, selected from the group consisting of fused and unfused C$_6$–C$_{22}$-aromatics and fused or unfused C$_5$–C$_{22}$-heteroaromatics which have at least one nitrogen, oxygen or sulfur atom in the ring;

R$_1$ and R$_2$ independently of one another are a hydrogen atom, a C$_1$–C$_8$-alkyl radical or an aryl radical Ar.

2. The process as claimed in claim 1, wherein the basic catalyst is an alkali metal amide, alkaline earth metal amide, alkali metal hydrocarbon or alkaline earth metal hydrocarbon.

3. The process as claimed in claim 1, wherein a mixture of at least two basic catalysts is used.

4. The process as claimed in claim 1, wherein the basic catalyst is employed in an amount of from 0.01 to 20 mol % based on the arylpiperazine of the formula (II).

5. The process as claimed in claim 1, wherein the aryl radicals Ar or Ar' independently of one another have up to 8 identical or different substituents selected from the group consisting of a hydrogen atom, a fluorine atom, a chlorine atom, a bromine atom, an iodine atom, $C_1$–$C_8$-alkyl, $C_1$–$C_8$-alkoxy, $C_1$–$C_8$-acyloxy, HO—, $O_2$N—, CN—, HOC(O)—, HC(O)—, HOS(O)$_2$—, $R^4$S(O)$_2$—, $R^4$S(O)—, $H_2$N—, $R^4$N(H)—, $R^4{}_2$N—, $R^4$C(O)N(H)—, $R^4$C(O)—, (OCH)HN—, Ar"C(O)—, ArC(O)O—, CF$_3$—, $H_2$NC(O)—, $R^4$OC(O)C(H)=C(H)—, Ar"$_2$P(O)—, $R^4{}_2$P(O)—, $R^4{}_3$Si— and heteroaryl radicals having 5 or 6 atoms in the aryl ring, $R^4$ is a $C_1$–$C_{12}$-alkyl radical and Ar" is fused or unfused $C_6$–$C_{22}$-aromatics or fused or unfused $C_5$–$C_{22}$-heteroaromatics which have at least one nitrogen, oxygen or sulfur atom in the ring.

6. The process as claimed in claim 2, wherein a mixture of at least two basic catalysts is used.

7. The process as claimed in claim 6, wherein the basic catalyst is employed in an amount from 0.1 to 5 mol % based on the arylpiperazine of the formula (II).

8. The process as claimed in claim 7, wherein aryl radicals Ar or Ar' independently of one another have up to 8 identical or different substituents selected from the group consisting of a hydrogen atom, a fluorine atom, a chlorine atom, a bromine atom, an iodine atom, $C_1$–$C_8$-alkyl, $C_1$–$C_8$-alkoxy, $C_1$–$C_8$-acyloxy, HO—, $O_2$N—, CN—, HOC(O)—, HC(O)—, HOS(O)$_2$—, $R^4$S(O)$_2$—, $R^4$S(O)—, $H_2$N—, $R^4$N(H)—, $R^4{}_2$N—, $R^4$C(O)N(H)—, $R^4$C(O)—, (OCH)HN—, Ar"(O)—, ArC(O)O—, CF$_3$—, $H_2$NC(O)—, $R^4$OC(O)C(H)=C(H)—, Ar"$_2$P(O)—, $R^4{}_2$P(O)—, $R^4{}_3$Si— and heteroaryl radicals having 5 or 6 atoms in the aryl ring, $R^4$ is a $C_1$–$C_{12}$-alkyl radical and Ar" is fused or unfused $C_6$–$C_{22}$-aromatics or fused or unfused $C_5$–$C_{22}$-heteroaromatics which have at least one nitrogen, oxygen or sulfur atom in the ring.

9. The process as claimed in claim 1, wherein the reaction is carried out at a temperature from 0 to 200° C.

10. The process as claimed in claim 8, wherein the reaction is carried out at a temperature from 10 to 150° C.

11. The process as claimed in claim 10, wherein the reaction is carried out at a temperature from 20 to 120° C.

* * * * *

UNITED STATES PATENT AND TRADEMARK OFFICE
CERTIFICATE OF CORRECTION

PATENT NO. : 6,313,297 B1  
DATED : November 6, 2001  
INVENTOR(S) : Herwig et al.

Page 1 of 1

It is certified that error appears in the above-identified patent and that said Letters Patent is hereby corrected as shown below:

Title page,
Item [73] Assignees "Assignees: Aventis Research & Technologies (DE); GmbH & Co. KG (DE)" should read as -- Assignee: Aventis Research & Technologies GmbH & Co. KG (DE) --.

Item [86], "§371 Date: Jun. 13, 2000" should read as -- §371 Date: July 13, 2000 --. and "§102(e) Date: Jun. 13, 2000" should read as -- §102(e) Date: July 13, 2000 --.

Column 10,
Line 9, "AR(O)-,..." should read as -- AR"C(O)-,.... --

Signed and Sealed this

Twenty-eighth Day of May, 2002

*Attest:*

JAMES E. ROGAN
*Director of the United States Patent and Trademark Office*

*Attesting Officer*